(12) United States Patent
Laxman et al.

(10) Patent No.: US 6,777,219 B2
(45) Date of Patent: Aug. 17, 2004

(54) PROCESS FOR THE PREPARATION OF ALKALINE PROTEASE

(75) Inventors: Ryali Seeta Laxman, Maharashtra (IN); Snehal Vijay More, Maharashtra (IN); Meenakshi Vilas Rele, Maharashtra (IN); Bommaraju Seeta Rama Rao, Maharashtra (IN); Vithal Venkatrao Jogdand, Maharashtra (IN); Mala Balachandra Rao, Maharashtra (IN); Vasanti Vishnu Deshpande, Maharashtra (IN); Ramachandra Boopathy Naidu, Tamil Nadu (IN); Panchatcharam Manikandan, Tamil Nadu (IN); Dilly Ashok Kumar, Tamil Nadu (IN); James Kanagaraj, Tamil Nadu (IN); Ramalingam Samayavaram, Tamil Nadu (IN); Natesan Samivelu, Tamil Nadu (IN); Puvanakrishnan Rengarajulu, Tamil Nadu (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/095,428

(22) Filed: Mar. 13, 2002

(65) Prior Publication Data

US 2003/0175899 A1 Sep. 18, 2003

(51) Int. Cl.⁷ ................................................. C12N 9/58

(52) U.S. Cl. ........................................ 435/223; 435/265
(58) Field of Search .......................................... 435/223

(56) References Cited

PUBLICATIONS

Computer Abs 1991–05310 Biotechds Sutar et al "A low molecular weight alkaline proteinase from *Conidiobolus coronatus*; protease purification and characterization" Biotechnol.Lett.; (1991) 13, 2, 119–24.*

Computer Abs 992–09419 Biotechds Sutar et al"Production of an alkaline proteinase from *Conidiobolus coronatus* and . . . protease preparation and charact" World J.Microbiol. Biotechnol.; (1992) 8, 3, 254–58.*

Computer Abs 93Δ1658 Scisearch Phadatare et al "High activity alkaline protease from *Conidiobolus–coronatus*." Enzyme and Microbial Technology, (Jan. 1993) vol. 15, No. 1, pp. 72–76. ISSN: 0141–0229.*

* cited by examiner

*Primary Examiner*—Herbert J. Lilling
(74) *Attorney, Agent, or Firm*—Burns, Doane, Swecker & Mathis, L.L.P.

(57) ABSTRACT

The present invention relates to a process for the preparation of alkaline protease using a fungal culture of the order entomophthorales and to the use of the said protease in the pretanning processes of leather manufacture.

6 Claims, No Drawings

PROCESS FOR THE PREPARATION OF ALKALINE PROTEASE

FIELD OF THE INVENTION

The present invention relates to a process for the preparation of alkaline protease. More particularly, it relates to the preparation of the said alkaline protease using a fungal culture of the order entomophthorales. The present invention also relates to an eco-friendly application of the said protease in the pretanning processes of leather manufacture. Still more particularly, it relates to soaking, dehairing and bating of skins as well as dehairing of hides in leather manufacture.

BACKGROUND OF THE INVENTION

Proteases are the single class of enzymes, which occupy a pivotal position with respect to their physiological and commercial applications. Of the industrial enzymes, 75% are hydrolytic in nature. Proteases represent one of the three largest groups of industrial enzymes and account for 60% of the total worldwide sale of enzymes. Proteases have a variety of applications mainly in the detergent, food and pharmaceutical industries [Rao, M. B., Tanksale, M., Ghatage, M. S., and V. V. Deshpande, (1998) Microbiology and Molecular Biology Reviews. Vol.62, 597]. In view of the recent trend of developing environmentally friendly technologies, proteases are envisaged to have extensive applications in leather manufacture and in several bioremediation processes.

Leather processing involves several steps such as soaking, dehairing, bating and tanning. The major building blocks of skin and hair are proteinaceous matter. Conventional methods of leather processing employ chemicals such as sodium sulphide and lime which are highly polluting. Use of enzymes as alternatives to chemicals has proved successful in improving leather quality and in reducing environmental pollution [Puvanakrishanan, R. (1993) Science Reporter, 30 58].

Proteases are also used for selective hydrolysis of non-collagenous constituents of the skins and for removal of proteins such as albumins, globulins, elastins and reticulins.

Conventional method of dehairing consists of swelling of skins or hides under extremely alkaline conditions using lime followed by treatment with sulphide to solubilize proteins in significant reduction in both quantity of wastewater and in the pollution load.

Approximately 50% of the enzymes used as industrial process aids are proteolytic enzymes [Gorey. T., and Reichelt, J.(1983) industrial Enzymology: the application of enzymes in industry, Nature Press, N.Y]. Proteolytic and amylolytic enzymes derived from various sources viz. microbial, animal and plant sources have been applied individually or in combination to produce effective dehairing of hides and skins. Proteolytic enzymes are more efficient in enzymatic dehairing than amylolytic enzymes and hence find wider application.

Animal proteases like pancreatin have been utilized for the depilation of pigskins at a pH of 8.0–9.0 at 37° C. with pretreatment using sodium sulphate and sodium thiosulfate [Felicjaniak, B. (1975) Pr.Inst. Przem. Skorzanego, 19, 77]. Jonczyk and Studniarski (1985) have shown that pigskins are dehaired in 4.5 at 37° C. using a system containing a pancreatic enzyme preparation, ammonium sulphate and sodium bisulfate [Jonczyk, G. W. and Studniarski.K (1985) Przegl. Skorzany. 40, 222].

Plant proteases such as those obtained form powdered leaves and barks of the Jawasee shrub, which contains rich amounts of a proteolytic enzyme, are used for dehairing hides and skins in the Indian States of Gujarat, Rajasthan and Madhya Paradesh and a process for the manufacture of grain garment leather using Jawasee protease has been described [Yeshodha, K., Dhar, S. C. and Santappa, M. (1978) Leath. Sci., 25, 36].

A pineapple protease is found to have maximum activity at pH 3.5–4.5 and good hide dehairing effects are obtained at pH 5.0–5.5 in the temperature range of 30–42° C. [Xia Y. (1982) Pige Keji 5,8]. Adewoye and Bangaruswamy (1984) have developed a single unit process for dehairing of hides using the neutral protease from the fruit of *Adenopus breviflorus* [Adewoye, R. O. and Bangaruswamy, S, (1984) Leder, 35, 78].

With the renewed emphaisis on biotechnology, microbial enzymes have received increasing attention and processes that involve versatile utilization of microbial metabolic machinery for the production of enzymes are currently being studied with great interest. Unlike animal and plant proteases Microbial proteases can be produced in large quantities and genetic manipulation to increase activity is easier. As is well known, microbial proteases are derived from a wide variety of yeasts, molds and bacteria.

Several processes are reported for the production of fungal enzyme depilants and bates. The influence of several cultural conditions and important nutritional factors on the formation of protease by *A. parasiticus* on cheap indigenous materials has been shown [Bose, S. M. and Dhar, S. C. (1958) Indian Patent No. 64354]. Markin has recommended the use of enzyme preparations from *A. oryzae* and *A. flavus* for depilation [Markin, I. V (1963) Kozh Obuvn., Prom-st., 5, 30]. Recently, a fungal alkaline protease from *A. flavus* has been developed in Central Leather Research Institute, India and it has been found to be effective in the dehairing of skins [Malathi, S. and Dhar, S. C. (1991) Appl. Environ. Mircrobiol. 57, 712; Malathi, S., Chakraborty, R., Parthasarathy, K., Ramanaiah, B., Gupta, K. B and Mitra R. B., (1991) J. Amer. Leather Assoc, 86, 33].

Enzymes derived form bacteria have gained much commercial interest because of their easy production capabilities by submerged cultivation, high yield of enzyme, short duration of production and easy recovery of the enzyme. Proteolytic enzymes derived from a large number of Bacillus species have been reported to be used in dehairing and bating of hides and skins [Toyoda, H. and Futami, A. (1962) Bull. Japan Assoc. Leath. Technol., 8,49]. Detailed studies on the use of enzymes from *Bacillus subtilis* have been carried out by Simoncini and coworkers [Simoncini, A. Del Pezzo, L. Meduri, A. (1967) Cuoio Pelli Mat Concianti, 43, 382; Simoncini, A and Tessitore (1971), Cuoio Pello mat Cocianti 47, 201; Hameed, A., Walt, M. A. and Evens, C. S. (1996) World j. Microbiol. Biotechnol. 12, 289; Hameed, A., Walt, M. A. and Evans, C. S. (1996) J. Ind. Microbiol., 17, 77; Hameed, A., Keshavarz, T and Evans, C. S. (1999) J. Chem. Technol. Niotechnol. 74, 5].

A multiple protease concentrate from the culture filtrate of *Streptomyces moderatus* has been used for dehairing studies. While the individual proteases have been found to be ineffective in dehairing, the crude protein concentrate is efficient in the dehairing of hides and skins [Chandrasekaran, S. and Dhar, S. C. (1983) J. Ferment. Technol., 61, 511]. A novel method of depilation in an acid medium containing certain Lactobacillus culture has been reported [Schlosser, L. Kelller, W., Hein, A. and Heidemann, E., (1986) J. Soc. Leath. Technol. Chem. 70, 163]. The cattle hides or grain splits of raw hides are treated at 32° C. in culture medium obtained by inoculation with a stock culture of Lactobacillus in a plastic vessel. The culture is gently mixed for 1 min, once in an hour and 99% dehairing has been observed after incubation over one and half days.

Most commercial alkaline proteases used in detergents and leather applications are of bacterial origin viz. Novo-Nordisk, Denmark; M/s SPIC, Chennai, India & M/s Textan Chemicals, Chennai, India. Enzymes of fungal origin are advantageous due to the ease of cell removal during downstream processing. Although application of fungal proteases in leather processing has been reported it has not been studied on a commercial scale [Godfrey, T. and S. West (1996) Ind . Enzymology 296].

Production of alkaline protease using *Conidiobolus coronatus* has been reported by Tatsuaki and Koshi wherein the production of the protease was reported in complex medium containing glucose, organic and inorganic nitrogen sources and the inorganic salts [Tokuyama Tatsuaki & Asano Koshi 1978, Chemical Abstract 89, 39182]. The conventional media used for the production of proteases contain various ingredients like starch and micronutrients like phosphates and inorganic salts.

OBJECTS OF THE INVENTION

The main object of the invention therefore is to provide a process for the preparation of alkaline protease active and stable at high pH and in short fermentation cycles.

Another object of the invention is to provide a process for the production of the said alkaline protease without using expensive ingredients.

Another object is to provide the said process using a fungal strain *Conidiobolus coronatus* using cheap and simple medium devoid of inorganic salt.

Yet another object is to provide an eco-friendly application of the said alkaline protease to leather manufacture particularly in pre-tanning processes.

Still another object is to provide application of a single protease to soaking, dehairing and bating process in the leather manufacture.

Still another object is to provide an eco-friendly application of the said alkaline protease to pretanning processes namely soaking, dehairing and bating in the leather manufacture wherein these processes is carried out using the protease provided by present invention either sequentially or separately irrespective of the mode of carrying out these processes.

SUMMARY OF THE INVENTION

Accordingly, the present invention provides a process for the preparation of alkaline protease which comprises growing a fungal strain *Conidiobolus conronatus* in a medium having pH 6.0 to 9.0, a carbon source and a nitrogen source under aerobic conditions in submerged culture, at a temperature ranging between 20 to 30° C., for a period ranging between 2 to 6 days, harvesting the medium and separating the enzyme in liquid phase.

In one embodiment of the invention, the fungal strain *Conidiobolus coronatus* used has been isolated from Anekal, fKarnataka, India, and deposited in American Type Cell Culture (ATCC) depository under Accession Number PTA-4132.

In another embodiment, the carbon source comprises sugars selected from the group consisting of glucose, fructose, sucrose and arabinose; sugar alcohols selected from the group consisting of glycerol, mannitol and sorbitol; polysaccharides such as starch and agricultural wastes selected from the group consisting of groundnut meal, wheat bran and rice bran.

In another embodiment, the nitrogen source is selected from the group consisting of peptone, tryptone, casamino acids, casein, meat extract, yeast extract, corn steep liquor, Soyameal and nitrogen-rich leguminous substrates such as gram flour.

In another embodiment, the fermentor media composition is selected from the group consisting of a carbon source and soyabean meal.

In a preferred embodiment of the invention, the fermentor media composition comprises glucose and soyabean meal.

The present invention also provides for application of the alkaline protease prepared as aforesaid to soaking the dried/dry salted skin of animals in aqueous solution of the enzyme optionally in presence of a preservative, at ambient temperature for 16 to 20 hrs.

In one of the embodiments, the concentration of the enzyme for soaking are in the range of 0/125 to 0.5% of raw weight of the skins.

In another embodiment the preservative comprises any conventional preservative used in the tanning industry.

In yet another embodiment, the concentration the preservative is present in an amount in the range of 0.005 to 0.01% of the raw weight of the skin.

The present invention also provides for application of the alkaline protease prepared as aforesaid to dehairing using the said protease enzyme, which comprises applying to the flesh side of the soaked skin a paste consisting of sodium sulphide, protease enzyme, a wetting agent and a suspension agent for a period of 12 to 20 hrs., or suspending the hides in a mixture containing protease, sodium sulphide and water for 20 to 30 hrs., and removing the hair by conventional methods.

In one of the embodiments, the concentration of sodium sulphide is in the range of 0.5 to 2% preferably 0.5%.

In another embodiment the wetting agent is a non-ionic detergent or a conventional detergent used in the tanning industry.

In still another embodiment the suspension agent is selected from the group consisting of kaolin, chalk paste and bentonite.

The present invention also provides for application of the alkaline protease prepared as aforesaid to bating the dehaired skins with solution of the protease enzyme at a pH in the range of 9 to 10.5 preferably at 9.5 for a period of 1 to 2 hrs.

In another embodiment of the invention, the production of enzyme is carried out by cultivating the fungal strain in a culture medium under aerobic conditions in submerged culture with shaking/aeration.

DETAILED DESCRIPTION OF THE INVENTION

The present invention provides a process for the preparation of alkaline protease which comprises growing a fungal strain *Conidiobotus coronatus* in a medium having pH 6.0 to 9.0, a carbon and a nitrogen source under aerobic conditions in submerged culture, at a temperature ranging between 20 to 30 C., for a period ranging between 2 to 6 days, harvesting the medium and separating the enzyme in liquid phase by conventional methods. The fungal strain *Conidiobolus coronarus* used has been isolated from Anekal, Karnataka, India and deposited in American type Cell Culture (ATCC) depository lacated at 10801 University Blvd., Manassas, Va. 20110-2209 on Mar. 11, 2002 under Accession Number PTA-4 132.

The carbon sources is generally selected from sugars, glucose, fructose, sucrose, arabinose; sugar alcohols exemplified be glycerol, mannitol, sorbitol; polysaccharides like starch and other agricultural wastes such as groundnut meal, wheat bran, rice bran etc. The nitrogen sources is peptone, tryptone, casamino acids, casein, meat extract, yeast extract, corn steep liquor,. Soyameal and nitrogen-rich leguminous substrates exemplified by gram flour. The fermentor media compositon is glucose and soyabean meal or any carbon source and soyabean meal.

The present invention also provides for application of the alkaline protease prepared as aforesaid to soaking the dried/dry salted skin of animals in aqueous solution of the enzyme optionally in presence of a preservative, at ambient temperature for 16 to 20 hrs.

In one of the embodiments, the concentration of the enzyme for soaking is in the range of 0/125 to 0.5% of raw weight of the skins.

In another embodiment the preservative used is a conventional preservative used in the tanning industry.

In yet another embodiment, the concentration the preservative is in the range of 0.005 to 0.01% of the raw weight of the skin.

The present invention also provides for application of the alkaline protease prepared as aforesaid to dehairing using the said protease enzyme, which comprises applying to the flesh side of the soaked skin a paste consisting of sodium sulphide, protease enzyme, a wetting agent and a suspension agent for a period of 12 to 20 hrs., or suspending the hides in a mixture containing protease, sodium sulphide and water for 20 to 30 hrs. and removing the hair by conventional methods.

In one of the embodiments, the concentration of sodium sulphide is in the range of 0.5 to 2% preferably 0.5%.

In another embodiment the wetting agent is non-ionic detergent or may be any conventional detergent used in the tanning industry.

In still another embodiment the suspension agent is such as kaolin, or chalk paste or bentonite.

The present invention also provides for application of the alkaline protease prepared as aforesaid to bating the dehaired skins with solution of the protease enzyme at a pH in the range of 9 to 10.5 preferably at 9.5 for a period of 1 to 2 hrs.

In a feature of the present invention, the production of enzyme is carried out by cultivating the fungal strain in a culture medium under aerobic conditions in submerged culture with shaking/aeration. In submerged culture the media composition essentially included sources rich in protein as exemplified by agricultural residues/wastes such as soyabean meal, groundnut meal, wheat bran, rice bran etc. Organic nitrogen sources in the form of peotone, yeast extract, tryptone, casein, casamino acids and meat extract can also be used for enzyme production. Medium for submerged alkaline protease production is dispersed in Erlenmeyer flasks and pH can be adjusted in the range of 6–9; preferably in the range of 6–7. Temperature for the enzyme production was between 20–30 C., preferably in range of 25–29 C. and shaker speed was adjusted between 180–220 rpm. Fermentation period varied from 2 to 6 days depending on the medium.

In another feature, the alkaline protease production under controlled conditions in fermentors (10–100L working volume) was carried out with aeration ranging from 0.5–1.5 vvm and agitation in the range of 200–600 rpm. Addition of inducers for protease production was carried out either in single or multiple lots. Cells were separated by filtration to obtain enzyme. Concentration of the culture supernatant was achieved either by membrane filtration or by salting out through addition of salts such as ammonium sulphate, sodium sulfate, sodium chloride etc.

In yet another feature, the protease activity has been expressed in terms of tyrosine equivalents. The reaction mixture contained an aliquot of suitably diluted enzyme solution and 10 mg Hammerstein casein in 0.1 M sodium carbonate buffer pH 10.0 in a total volume of 2 ml. after incubation at 40° C. for 10 min, the reaction was terminated by the addition of 3 ml of 5% trichloroacetic acid (acidified with concentrated hydrochloric acid). The precipitate formed was filtered through Whatman No. 1 filter paper after standing for 30 min at room temperature. The absorbance of trichloracetic acid soluble fraction was measured at 280 nm. Milligrams of tyrosine produced is calculated from a precalibrated graph of absorbance at 280 nm against tyrosine concentration and the unit is expressed as mg of tyrosine/ml enzyme/min at 40° C.

In still another feature, the alkaline protease was evaluated for soaking of dried/or dry salted goatskins. The enzyme was found to be effective in soaking in the enzyme concentrating range of 0.125 to 0.5% with an optimum around 0.25%; in a pH range of 8–10 with an optimum around 9. Soaking could be performed for 16–20 h with best results in 18 hrs. The soaking with fungal enzyme resulted in opening up of collagen bundles without any hair follicles and hair shafts while soaking with water along with wetting agent showed moderate presence of epidermis. Soaking with water alone resulted in compact dermis and revealed hair shaft with glands. Soaking with fungal enzyme resulted in 15–25% increase in moisture content with no significant changes in chemical and physical properties.

In still another feature the alkaline protease was found to be effective in dehairing with enzyme concentrations ranging from 0.5 to 2.5% (w/w tyrosine); sulphide concentrations ranging from 0.5 to 2.0%; pH varying between 7 to 10 and treatment times varying from 12 to 20 h. Visual assessment studies of enzyme dehaired pelts revealed that hair in the neck portion was completely removed. There was no short-hair and the pelts were more whilter than controls where dehairing was carried out using conventional methods. Visual assessment of dyed crusts also revealed that the leathers were of comparable quality to those produced by chemical methods. Physical testing results showed that the leathers obtained using alkaline protease were comparable to those obtained by lime and sulphide. Histological studies of the dehaired pelts produced using alkaline protease revealed that epidermis was totally lost with partly opened collagen fibre bundles without any short hairs and hair bulbs while conventional dehairing showed short hairs and dermis having dense collagen bundles.

In still another feature, the alkaline protease was found to be effective in dehairing of hides with enzymes concentrations ranging from 1.5 to 3.0% (w/w tyrosine); sulphide concentration ranging from 1.5 to 3.0% pH, varying between 7 to 10 and treatment time varying from 18 to 30 hrs. Visual assessment studies of the enzyme dehaired pelts showed that hair in the neck portion was completely removed. Visual assessment after dyeing showed that characteristics of grain smoothness, softness and flexibility were of comparable quality to those leathers produced by lime-sodium sulphide dehairing. Physical testing studies revealed that the physical properties of the crusts obtained by enzymatic dehairing were found to be comparable to those crusts obtained by lime-sulphide dehairing.

In another feature, the alkaline protease was suitable for bating in pH range 8.5 to 9.5; enzyme concentrations varying from 0.125 to 1.0% (w/w) and treatment times varying from 30 min. to 2 hrs. Visual assessment revealed that the alkaline protease bated skins were found to have silky grain with good flaccidity. In addition, they were found to be clean and air pocket test was found to be positive. Histological studies confirmed the removal of epidermis and showed the opening up of the fibre structure. The skins were found to have good strength properties when compared to control where no bating was done. This showed that the bating operation using fungal enzyme did not affect the strength properties of the leather.

The process of the invention is described herein below with examples, which are illustrative and should not be constructed as limiting the scope of the invention in any manner whatsoever.

EXAMPLE—1

This example illustrates the preparation of the protease. Spores from 4 days old melt extract, glucose, yeast extract, peptone (MGYP) slant were transferred into 250 ml production medium consisting of (g/L) glucose-10, yeast extract-3, and soyabean meal 20 in 1L capacity Erlenmeryer flasks. The flasks were incubated at 28C. under shaking on shaker at 220 rpm for 3 days. The activity in the cell free both, after three days was 18 mg Tyr/ml/min.

EXAMPLE—2

This example illustrates the application of enzyme for soaking (goatskins). 15 dry salted goatskins of approximately 1 kg each were tested for soaking in pit method. The skins were washed with 300% water for 5 min. Then, the skins were transferred into the soaking bath containing 0.01% preservative; 0.25% (w/w) alkaline protease and 400% water. All the weights are based on the weights of the skin. The pH of the soak solution was adjusted to 9.0 with sodium carbonate and soaking was performed overnight (18 h). The skins were further processed for dehairing, bating etc. by conventional methods and subjected to physical testing, chemical analysis and histological studies.

Results: The soaking with fungal enzyme resulted in opening up of collagen bundles without any hair follicles and hair shafts while soaking with water along with wetting agent showed moderate presence of epidermis. Soaking with water alone resulted in compact dermis and revealed hair shaft with glands. Soaking with fungal enzyme resulted in 15–25% increase in moisture content with no significant changes in chemical and physical properties.

EXAMPLE—3

This example illustrates the application of enzyme for dehairing (goatskins) 10 wet salted goatskins of approximately 1 kg each were used for dehairing. The presoak was carried out with 300% water in pit method. The main soak contained 0.01% non-ionic wetting agent. It was handled twice n hour for two hours. Later, the skins were given alkali treatment by soaking in 300% water adjusted to pH 10.0 (with sodium carbonate) for two hours.

The skins were processed for dehairing studies. The enzyme was mixed with sodium sulphide, kaolin, and wetting agent and applied as paste on the flesh side of the skin, piled for 20 h and dehairing was carried out in usual manner. The enzyme paste contained 2% alkaline protease (tyrosine), 0.5% sodium sulphide, 0.1% wetting agent, 10% kaolin and sodium carbonate buffer of pH 0.1% to make into a paste.

Results: Visual assessment studies of enzyme dehaired pelts revealed that hair in the neck portion was completely removed. There was no short hair and the pelts were more whither than controls where dehairing was carried out using conventional methods. Visual assessment of dyed crusts also revealed that the enzyme treated leathers were of comparable quality to those produced by chemical methods. Physical testing results showed that the leathers obtained using alkaline protease were comparable to those obtained by lime and sulphide. Histological studies of the dehaired pelts produced using alkaline protease revealed that epidermis was totally lost with partly opened collagen fibre bundles without any short hairs bulbs while conventional dehairing showed short hairs and dermis having dense collagen bundles.

EXAMPLE—4

This example illustrates the application of enzyme for dehairing of cow hides. 40 kg of wet soaked hides were used for the deharing experiment. After thorough washing, the hides were given alkali treatment by soaking for 6 hrs in 300% water adjusted to pH 10.0 using sodium carbonate. The hides were then immersed in a tub containing 3% alkaline protease (w/w tyrosine), 2% sodium sulphide and 100% water. After periodical handling, dehairing was carried out after 24 hrs.

Results: Visual assessment studies of the enzyme dehaired pelts showed that hair in the neck portion was completely removed. Visual assessment after dyeing showed that characteristics of grain smoothness, softness and flexibility were of comparable quality to those leathers produced by lime-sodium sulphide dehairing. Physical testing studies revealed that the physical properties of the crusts obtained by enzymatic dehairing were found to be comparable to those crusts obtained by lime-sulphide dehairing.

EXAMPLE—5

This example illustrates the application of enzyme for bating of goatskins. Ten wet selted goatskins of 1 kg each were used for bating studies. After conventional soaking, dehairing was carried out by lime and sulphide method. Partial deliming was carried out using ammonium sulphate at pH of 9.5. Bating was carried out by drumming the skins for 1.5 hrs. with 100% float at pH 9.5 and 0.25% enzyme.

Results: Visual assessment revealed that the fungal enzyme bated skins were found to have silky grain texture good flaccidity. In addition, they were found to be clean and air pocket test was found to be positive. Histological studies confirmed the removal of epidermis and showed the opening up of the fibre structure. The skins were found to have good strength properties when compared to control where no bating was done. This showed that the bating operation using fungal enzyme did not affect the strength properties of the leather.

ADVANTAGES OF THE PRESENT INVENTION

1. The enzyme of the present invention has wider pH activity in the range of 7.0-12.0 and temperature stability in the range of 2514 50° C.

2. The enzyme of the present invention is found to be stable in the presence of commercial detergents and surfactants.
3. The enzyme of the present invention is found to be effective for soaking, dehairing and bating of skins as well as for dehairing of hides.
4. The enzyme of the present invention can be used for the process of soaking, dehairing and bating operations carried out either in succession or separately irrespective of the mode of previous or successive operations.

We claim:

1. A process for the preparation of alkaline protease which comprises growing a fungal strain *Conidiobolus coronatus* isolated from Anekal, Karnataka, India and deposited in American Type Cell Culture (ATCC) depository under Accession Number PTA-4132, in a medium having pH 6.0 to 9.0, a carbon source and a nitrogen source under aerobic conditions in submerged culture, at a temperature ranging between 20 to 30° C., for a period ranging between 2 to 6 days, harvesting the medium and separating the enzyme in liquid phase.

2. A process as claimed in claim 1 wherein the carbon source comprises sugars selected from the group consisting of glucose, fructose, sucrose and arabinose; sugar alcohols selected from the group consisting of glycerol, mannitol and sorbitol; polysaccharides and agricultural wastes selected from the group consisting of groundnut meal, wheat bran and rice bran.

3. A process as claimed in claim 1 wherein the nitrogen source is selected from the group consisting of peptone, tryptone, casamino acids, casein, meat extract, yeast extract, corn steep liquor, Soyameal and nitrogen-rich leguminous substrates.

4. A process as claimed in claim 1 wherein the fermentor media composition is selected from the group consisting of a carbon source and soyabean meal.

5. A process as claimed in claim 4 wherein the fermentor media composition comprises glucose and soyabean meal.

6. A process as claimed in claim 1 wherein the production of enzyme is carried out by cultivating the fungal strain in a culture medium under aerobic conditions in submerged culture with shaking/aeration.

* * * * *